(12) United States Patent
Park et al.

(10) Patent No.: US 8,168,422 B2
(45) Date of Patent: May 1, 2012

(54) MICROORGANISM PRODUCING INOSINE AND METHOD OF PRODUCING INOSINE USING THE SAME

(75) Inventors: Young-hoon Park, Gyeonggi-do (KR); Kwang-myung Cho, Gyeonggi-do (KR); Hee-jong Lee, Gyeonggi-do (KR); Jin-nam Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 327 days.

(21) Appl. No.: 12/522,004

(22) PCT Filed: Jan. 15, 2008

(86) PCT No.: PCT/KR2008/000236
§ 371 (c)(1),
(2), (4) Date: Jul. 2, 2009

(87) PCT Pub. No.: WO2008/088156
PCT Pub. Date: Jul. 24, 2008

(65) Prior Publication Data
US 2010/0081173 A1    Apr. 1, 2010

(30) Foreign Application Priority Data
Jan. 15, 2007    (KR) .................. 10-2007-0004341

(51) Int. Cl.
*C12P 19/40* (2006.01)
*C12N 9/00* (2006.01)
*C12N 1/20* (2006.01)
*C12N 15/00* (2006.01)
*C07H 21/04* (2006.01)

(52) U.S. Cl. .... 435/252.3; 435/88; 435/183; 435/320.1; 536/23.2

(58) Field of Classification Search .................. None
See application file for complete search history.

(56) References Cited

U.S. PATENT DOCUMENTS

| 3,616,207 | A | 10/1971 | Yoneda et al. |
| 3,668,071 | A | 6/1972 | Nara et al. |
| 6,962,805 | B2 | 11/2005 | Asakura et al. |

FOREIGN PATENT DOCUMENTS

| EP | 1447442 A1 | 8/2004 |
| KR | 10-1988-0002418 | 11/1998 |
| KR | 10-2005-0059640 | 6/2005 |
| KR | 10-0694427 B1 | 3/2007 |
| WO | WO 00/18935 | 4/2000 |
| WO | WO 2005/023850 A2 | 3/2005 |

OTHER PUBLICATIONS

Accession AY603360. Mar. 29, 2006.*
Liu et al. World J Gastroenterol. Dec. 15, 2004;10(24):3683-7.*
Written Opinion issued May 2, 2009 in PCT/KR2008/000236.
Search Report issued May 2, 2009 in PCT/KR2008/000236.
European Search Report issued Mar. 18, 2010 in EP application serial No. EP 08704775 (PCT/KR2008/000236).
Rittmann et al. (Aug. 2005) Applied and Environmental Microbiology, 71(8):4339-4344 "Phosphate starvation-inducible gene *ushA* encodes a 5' nucleotidase required for growth of *Corynebacterium glutamicum* on media with nucleotides as the phosphorus source".
Petersen and Meller (Jan. 2001) Journal of Biological Chemistry 276(2):884-894 "The RihA, RihB, and RihC Ribonucleoside hydrolases of *Escherichia coli*: Substrate specificity, gene expression, and regulation".
Kim et al. (Apr. 2006) Microbiology, 152:1169-1177, "Genes encoding ribonucleoside hydrolase 1 and 2 from *Corynebacterium ammoniagenes*".
Kotani et al. (1978) Agric. Biol. Chem., 42(2):399-405, "Inosine Accumulation by Mutants of *Brevibacterium ammoniagenes* Strain Improvement and Culture Conditions".
Matsui et al. (1982) Agric. Biol. Chem., 46(9):2347-2352, "5'-Nucleotidase Activity in Improved Inosine-producing Mutants of *Bacillus subtilis*".
Arts et al. (Jun. 1998) J. Virology, 72(6):4858-4865, "3'-Azido-3'-Deoxythymidine (AZT) Mediates Cross-Resistance to Nucleoside Analogs in the Case of AZT-Resistant Human Immunodeficiency Virus Type 1 Variants".

* cited by examiner

*Primary Examiner* — Christian Fronda
(74) *Attorney, Agent, or Firm* — Swanson & Bratschun, L.L.C.

(57) ABSTRACT

The present invention relates to a microorganism producing inosine, which is one of purine nucleoside, an important material for 5'-inosinic acid synthesis, and method for producing inosine using the same. More particularly, the present invention relates to a recombinant microorganism of *Corynebacterium* genus producing inosine at high concentration by inactivating the gene encoding nucleoside hydrolase II and by enhancing the expression of the gene encoding 5'-nucleotidase, which still retains the characteristics of *Corynebacterium ammoniagenes* CJIP2401 (KCCM-10610).

4 Claims, 2 Drawing Sheets

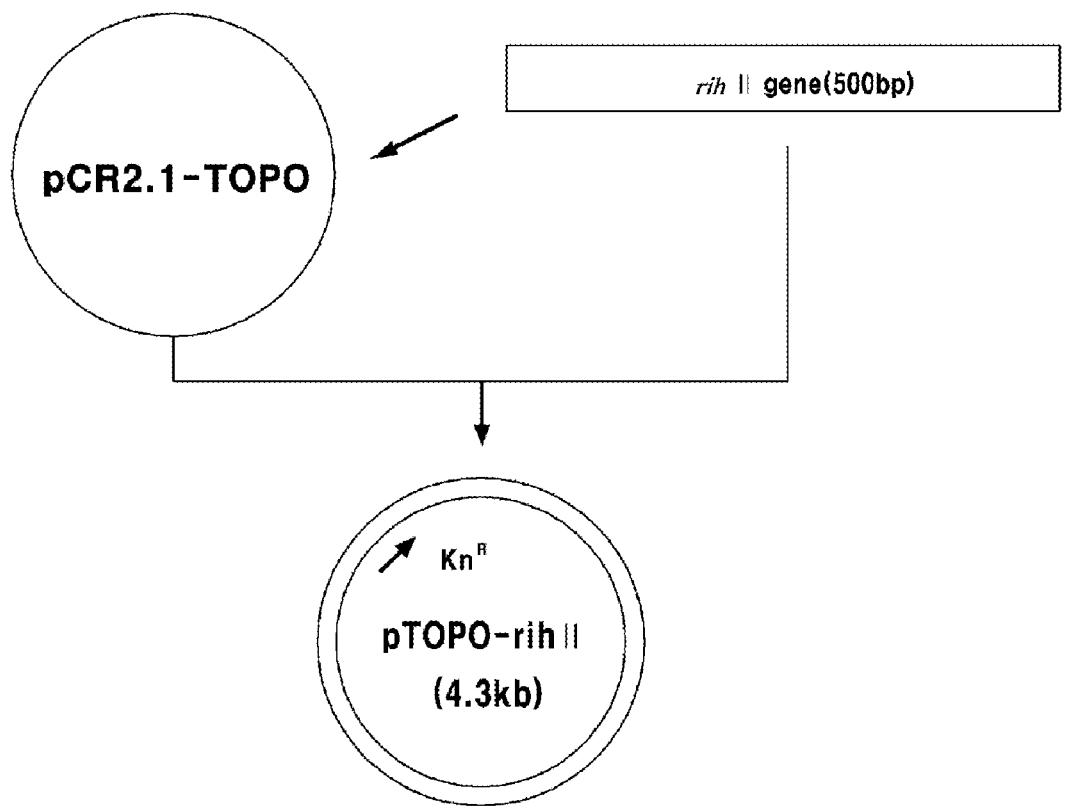
[Fig. 1]

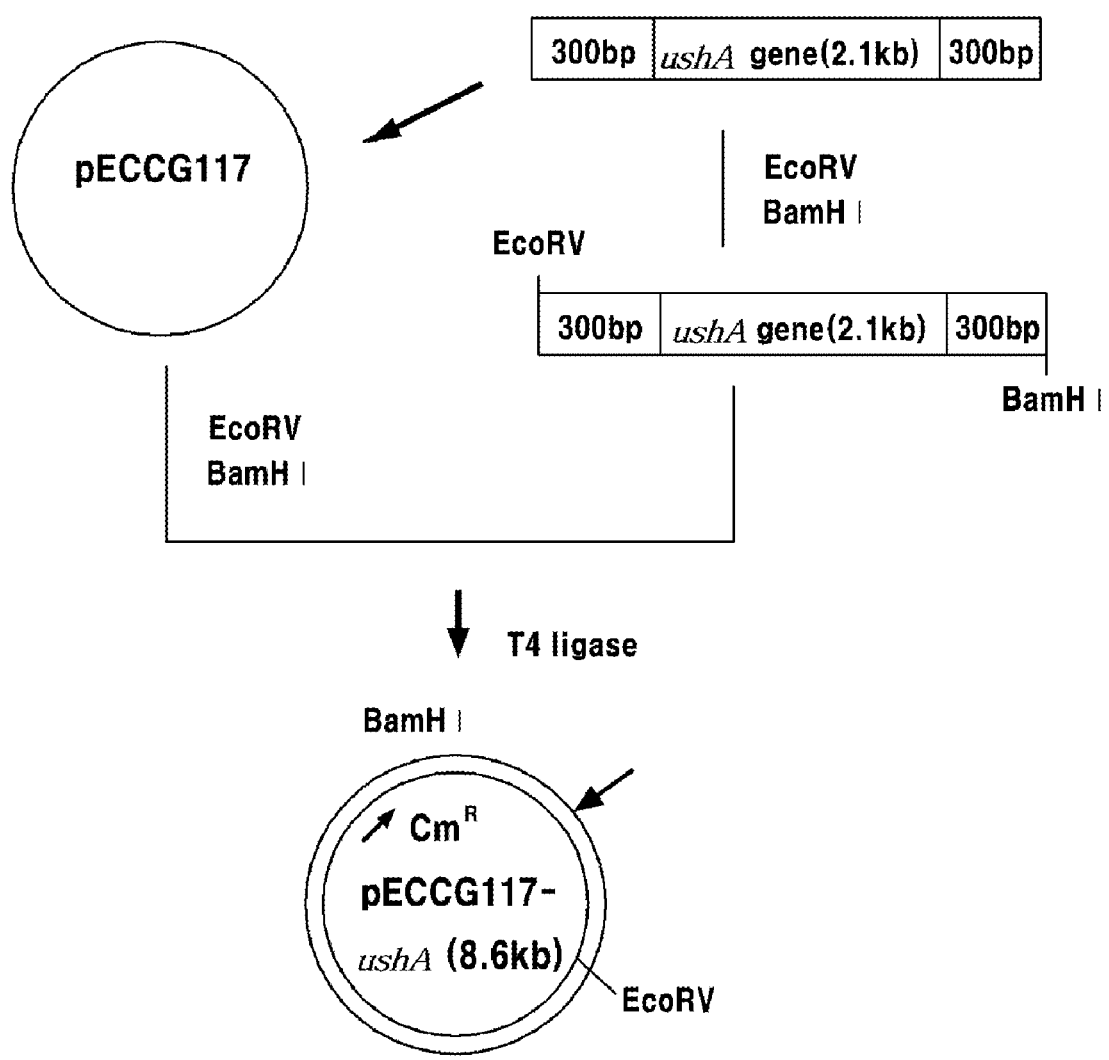
[Fig. 2]

SEQUENCE LISTING

```
<160> NUMBER OF SEQ ID NOS: 6

<210> SEQ ID NO 1
<211> LENGTH: 927
<212> TYPE: DNA
<213> ORGANISM: Corynebacterium ammoniagenes

<400> SEQUENCE: 1
atgaagatga ttttagatct agacaccggt atcgatgatg cctttgcgtt ggcctatgcc      60
atcgcacacc cgggtatcga tttgattggt gtcaccggaa cttatggcaa tgtcaccatt     120
gaacaaggca tggccaatac ccaggcactg ttgacgctac tgggcgcagc cgatgtgccc     180
gtatatgccg gacgcgctat cgatggcttt gaggtatctg aagcctctgc tcgtattcac     240
gggcgcaatg gcgtgggtga ggtagatatc gctgcagatg atgcgcaatc tgctggcgat     300
gcacttgaat ttttaagcga agcagcggcg aaatacggcg atgatttggt gatcgttccc     360
accggcgcgc aaacgacgct tgcgcgggct ttagaaaaag atcctgcatt gcgaggcatt     420
cgcatggtca gcatgggcgg cgccttaacc gtcccgggaa atgtgtcacc agcggctgag     480
```

| | |
|---|---|
| gcaaatatct cccaggaccc agtctcttcc aacactgtgt accagttggc tgaggatatg | 540 |
| accatggtgg gcttggatgt cactatgcaa acacagctca cacgtgctga ggcggattcg | 600 |
| tggcggggaa cgccagctgg agatgtcttt gctgatatgg ccggctatta catcgacgct | 660 |
| tatcaggaaa ataatccgca catggatggc tgcgccttgc atgacccgtt ggccgtggcg | 720 |
| gttgcagctg atcctgactt ggtggattgt ttgattcttc ccctgcaggt cgataccgaa | 780 |
| ggccccacca ttggtcgcac aattggacgg tgggatggct ctgaggtaga aacccgtgta | 840 |
| gccgttgggg taaacgtgga tagtttcgtg ccggatttca tcgacaagct ggcgcaacta | 900 |
| tttggacgat tggtccaaaa ccagtaa | 927 |

<210> SEQ ID NO 2
<211> LENGTH: 2115
<212> TYPE: DNA
<213> ORGANISM: Corynebacterium ammoniagenes

<400> SEQUENCE: 2

| | |
|---|---|
| gtgtctaagt ttcgccgttt tggccgtctg ctggctgcaa ccaccgtatc cgccaccatc | 60 |
| gtagttggcg cgcccgtagc ctttggtcaa gaagataatg ttgttgattt ctcagtcacc | 120 |
| aatatcactg acttccatgg ccacctttct acgcaggagg ctgacgctcc tgatgccaac | 180 |
| tcagagatgg gggcggccaa gctcaaggaa ctgattgagt acgttaatca ggaccaggaa | 240 |
| tacatcatga ctacctccgg cgataacgtc ggcggtagcg ctttcgtctc ggcaatcgct | 300 |
| gatgatgagc caaccctaga tgtcctcaac atgctcggcg ttgacgtctc tgcggtaggt | 360 |
| aaccatgaat tcgaccgcgg ctatgacgat ttgctcggtc gtattgctga aaaatccgcc | 420 |
| tacccattgc tgggcgcgaa tgtcacctta aacggtgaac cgatgttgga tgcttcctac | 480 |
| gttcaagaaa ttgacggcgt caaggtggga tttgtcggta ctgtgaccac cttgactaag | 540 |
| gacaaggtcg caccatccgc agttgaaggt gtggagtttt ctgaccccgt cgaggctacg | 600 |
| aataaggaat ctgaccgtct gaaggaatct ggcgaagcag acgttgttgt agcgctcatg | 660 |
| cacgaggacg cgcagcagta cgctgctggc ttcaacaaca atgtggatat cctttttcgga | 720 |
| ggcgactctc accagcgctc gcagggcatc atcgaacgtg atggtgcgca gccactgcac | 780 |
| tgggcgcagg gcatgaata tggcaaggtt ctccaagacg ccgatatttc ctttaacaag | 840 |
| gacaccggcg aaattgagtc cgtcgaaatc acccagtacg accgctcgat gcctgaggtt | 900 |
| gaagcactag cccctgatgc agaaattgcc gctcgcgtgg cagccgctga ggcagaagct | 960 |
| gaagagcttg gagctaaagt tgtcggccag atggaccgcg ctactttccg tggtcaagat | 1020 |
| gagggcgcag gagcggggag caaccgcggt gttgaatcta cgttgaactc gctaattgct | 1080 |
| gatgccaacc gcgcatcagt tgctaaggcg actggtgcgg acgtggattt gggcattatg | 1140 |
| aatgctggtg gcgtacgtgc tgaccttcct gcaggcgatg tcactttcca ggatgtgctt | 1200 |
| accgtgcagc ctttcggcaa ttcgattgca tacggcactt tgaccggcca agatattttg | 1260 |
| gatgctttgg aagctcagtg gcagccagga tcgtctcgtc cacgcttggc tttgggtcta | 1320 |
| tctgctggat ttgagtacgc ctacgaccca actgcagagc aaggccagcg cgttatctcc | 1380 |
| gcgaccttgg atggcgaaga aattgaccca tcagcggaat acactgttgc aacttccacg | 1440 |
| ttcctcttcg atggtggcga caacttcgca tctctggcca atgtccaaaa cctcactgac | 1500 |
| gtgggctaca tggactactc agttctcaat gactacatca aagatggcgc agaggtacag | 1560 |
| gaaggccagt ctgatatcgg tatcagcacc gaaggcaccc tggcagctgg tgaagaagtt | 1620 |
| accttcaacc tcacctcgct taactacact atggaagaag atccacaagc caccacagcg | 1680 |

-continued

```
accgtcaccg tgggcgacgt gcaagaaacc gccgatatcg acgctcagtg gaatgctgaa    1740
gaagatccgc agaagaatga atttggccgt gctagcgtaa cgctgactct gccagaggac    1800
attgaggaaa ccgacttggt taccgtaacc accgatgccg gcaccgagat tactgtgccg    1860
ctgagggcct tgggcaccaa cgagggcacg gacggcggct ccaatcctgg cagcagcgca    1920
cctggcacag gtaagggctc ttctcggggt gcttcggctg ctgcaggaat cgctggagtg    1980
ttggcagcga ttgcgggcat cgccgcgttt attggtctga acggtcagtt tgatcagttc    2040
atcccagcta acatgcagcg cgctcttggt gacctgcgca gtcagctcaa cgaggttagc    2100
cacatcaaat tctag                                                     2115
```

```
<210> SEQ ID NO 3
<211> LENGTH: 20
<212> TYPE: DNA
<213> ORGANISM: Artificial Sequence
<220> FEATURE:
<223> OTHER INFORMATION: primer rih II-F

<400> SEQUENCE: 3
tgctggcgat gcacttgaat                                                  20

<210> SEQ ID NO 4
<211> LENGTH: 21
<212> TYPE: DNA
<213> ORGANISM: Artificial Sequence
<220> FEATURE:
<223> OTHER INFORMATION: primer rih II-B

<400> SEQUENCE: 4
tgtgcgacca atggtggggc c                                                21

<210> SEQ ID NO 5
<211> LENGTH: 24
<212> TYPE: DNA
<213> ORGANISM: Artificial Sequence
<220> FEATURE:
<223> OTHER INFORMATION: primer ushA -F

<400> SEQUENCE: 5
gtgtctaagt ttcgccgttt tggc                                             24

<210> SEQ ID NO 6
<211> LENGTH: 34
<212> TYPE: DNA
<213> ORGANISM: Artificial Sequence
<220> FEATURE:
<223> OTHER INFORMATION: primer ushA -B

<400> SEQUENCE: 6
gccggatccc tagaatttga tgtggctaac ctcg                                  34
```

MICROORGANISM PRODUCING INOSINE AND METHOD OF PRODUCING INOSINE USING THE SAME

RELATED APPLICATIONS

This application is a 35 U.S.C. §371 national phase application of PCT/KR2008/000236 (WO 2008/088156), filed on Jan. 15, 2008, entitled "Microorganism Producing Inosine and Method of Producing Inosine Using the Same," which application claims the benefit of Korean Patent Application Serial No. KR 10-2007-0004341, filed on Jan. 15, 2007. Each of these applications is specifically incorporated herein by reference in its entirety.

TECHNICAL FIELD

The present invention relates to a microorganism producing inosine, one of purine nucleosides which are very important materials for 5'-inosonic acid synthesis, and method for producing inosine using the same. More particularly, the present invention relates to a recombinant microorganism of Corynebacterium genus producing inosine at high concentration, in which the characteristics of Corynebacterium ammoniagenes CJIP2401 (KCCM-10610) are exhibited, the gene encoding nucleoside hydrolase II (referred to 'rih II' hereinafter) is inactivated and expression of the gene encoding 5-nucleotidase (referred as 'ushA' hereinafter) is enhanced, and method for producing inosine using the same.

BACKGROUND ART

As a nucleoside synthesis-related enzyme, nucleoside hydrolase II is known to be involved in the degradation of nucleoside and 5'-nucleotidase is known to be involved in the nucleoside synthesis.

A gene encoding Nucleoside hydrolase II is the gene encoding the enzyme catalyzing ribose and corresponding bases, which are purine and pyrimidine, irreversibly, in salvage pathway of nucleoside. This gene contains a 1326 bp nucleoside sequence and encodes a protein of 308 amino acids and has substrate-specificity to both of purine and pyrimidine nucleosides (Microbiology, 2006, vol. 152, p 1169-1177).

A gene encoding 5'-nucleotidase is the gene encoding the enzyme catalyzing dephosphorylation of nucloeside such as AMP, GMP, IMP and XMP in nucleoside biosynthesis pathway (de novo pathway). This gene encodes a protein of 705 amino acids.

Inosine is an important substrate for the chemical synthesis and synthesis by enzyme transfer of 5'-inosinic acid which is in the lime light as a flavor-enhancing seasoning. Also, inosine is an intermediate of nucleic acid biosynthesis, which is not only an important physiological factor in animals and plants but also applied in various fields including food and medicinal industries. Nucleoside and its derivatives have been reported to have many usages as antibiotic, anti-cancer and anti-viral substances (J. Virol, vol; 72, pp 4858-4865).

The conventional method to produce inosine is direct fermentation using such microorganism as Bacillus (Agric. Biol. Chem., 46, 2347 (1982); Korean Patent No. 27280) or Corynebacterium ammoniagenes (Agric. Biol. Chem., 42, 399 (1978)), or thermal decomposition of 5'-inosinic acid (Japanese Laid-off Patent Publication No. S43-3320). However, the thermal decomposition requires massive heat, which makes it not practical. According to the direct fermentation, activity of the strain producing inosine is very low, so that production cost increases and fermentation takes longer, resulting in the low productivity.

To produce inosine by direct fermentation using a microorganism at high concentration with high yield, it is very important to develop a strain that is appropriate for the accumulation of inosine at high concentration in its culture broth.

The present inventors studied persistently to produce inosine with high productivity/high yield by direct fermentation using a microorganism. And at last, the present inventors completed this invention by confirming that the microorganism producing 5-inosonic acid could produce inosine with high productivity/high yield when rih II gene encoding nucleoside hydrolase II is inactivated and ushA gene encoding 5'-nucleotidase is enhanced.

DISCLOSURE OF INVENTION

Technical Problem

The present invention is established based on the above finding. Therefore, it is an object of the present invention to provide a recombinant microorganism of Corynebacterium genus wherein rih II gene encoding nucleoside hydrolase II is inactivated and the expression of ushA gene encoding 5'-nucleotidase is enhanced.

It is another object of the present invention to provide a method for producing inosine using the above microorganism.

Technical Solution

The above objects and other objects of the present invention can be achieved by the following embodiments of the present invention.

The present invention is described in detail hereinafter.

To achieve the objects of the invention, the present invention provides a microorganism having nucleoside productivity by manipulating the genes involved in nucleoside synthesis pathway of CJIP2401 (KCCM-10610), the mutant strain of Corynebacterium ammoniagenes ATCC 6872 that is able to accumulate 5'-inosinic acid at high concentration.

The parent strain used in the present invention, Corynebacterium ammoniagenes CJIP2401 (KCCM-10610) [Korean Patent Publication No. 10-2004-0099466], is the mutant strain of Corynebacterium ammoniagenes MP377 (KFCC11141). The mutant strain of Corynebacterium ammoniagenes MP377 (KFCC11141) [Korean Patent Application No. 10-2000-0013303] is originated from Corynebacterium ammoniagenes KFCC-10814 [Korean Patent No. 127853], the mutant strain of Corynebacterium ammoniagenes 6872. Therefore, the microorganism of the present invention shares the major characteristics explained below and has similar effects with Corynebacterium ammoniagenes CJIP2401 (KCCM-10610).

1) Adenine auxotroph
2) Guanine leaky type
3) Biotin auxotroph
4) sensitivity to Lysozyme 8 g/ml
5) resistant to 3,4-dihydroproline 3500 g/ml
6) resistant to 6-mercaptopurine 300 g/ml
7) resistant to 5-fluorotryptophan 10 mg/1

In this invention, rih II gene encoding the nucleoside hydrolase II was isolated from the wild type Corynebacterium ammoniagenes ATCC 6872 and preferably had the sequence represented by SEQ. ID. NO: 1.

In this invention, ushA gene encoding 5'-nucleotidase was isolated from the wild type *Corynebacterium ammoniagenes* ATCC 6872 and preferably had the sequence represented by SEQ. ID. NO: 2.

The present invention provides a recombinant microorganisms of *Corynebacterium* genus in which rih II gene encoding nucleoside hydrolase II protein is inactivated.

The present invention also provides a recombinant microorganism of *Corynebacterium* genus in which rih II gene encoding nucleoside hydrolase II protein is inactivated and the expression of ushA gene encoding 5'-nucleotidase is enhanced.

In this invention, the "inactivation" can be induced by any inactivation method known to those in the art. The term "inactivation" herein intends to mean that the expression of rih II gene encoding the nucleoside hydrolase II is reduced to a low level compared to the wild type strain, or genes that are not expressed and genes that express products having no activity or reduced activity in spite of being expressed are produced.

In this invention, the "inactivation" can be induced by one or more mutation methods selected from the group consisting of insertion of one or more base pairs in rih II gene, deletion of one or more base pairs in the gene, transition or transversion of base pairs by inserting nonsense codon in the gene.

In a preferred embodiment of the present invention, the microorganism containing the inactivated gene can be obtained by culturing a microorganism of *Corynebacterium* genus transformed with the vector containing a part of the rih II gene.

The part of the gene can be synthesized by using primers represented by SEQ. ID. NO: 3 and NO: 4.

In this invention, the rih II gene was inactivated by the insertion of a recombinant vector into *Corynebacteria*. However, instead of the recombinant vector, any known method including virus infection can be used to inactivate rih II gene, but not always limited thereto.

In this invention, the enhancement of the gene expression can be performed by any conventional method known to those in the art. Herein, the reinforcement of gene expression means the up-regulation of ushA gene encoding 5'-nucleotidase, compared with the wild type strain.

In this invention, the enhancement of the gene expression is induced by activation of the entire expression system containing the promoter region of ushA gene encoding 5'-nucleotidase.

In a preferred embodiment of the present invention, the microorganism containing the enhanced gene can be obtained by culturing a microorganism of *Corynebacterium* genus transformed with the vector containing the sequence represented by SEQ. ID. NO: 2 to express the entire expression system including the promoter region of ushA gene encoding 5'-nucleotidase.

The present invention further provides *Corynebacterium ammoniagenes* CJIG650 (Accession No: KCCM-10828P) having inactivated rih II gene and producing 5'-inosinic acid and inosine at high concentration, which is the mutant strain of *Corynebacterium ammoniagenes* CJIP2401 (KCCM10610).

The present invention also provides *Corynebacterium ammoniagenes* CJIG651 (Accession No: KCCM-10829P) having inactivated rih II gene and enhanced ushA gene and producing inosine at high concentration, which is the mutant strain of *Corynebacterium ammoniagenes* CJIG650 (KCCM-10828P).

The present invention also provides a method for producing inosine at high concentration with high yield by culturing *Corynebacterium ammoniagenes* CJIG650 (KCCM-10828P) and CJIG651 (KCCM-10829P) and accumulating inosine in the culture broth.

The construction process of the strain of the present invention is as follows.

Sequencing was performed with chromosome of a microorganism of *Corynebacterium* genus producing 5'-inosinic acid for example *Corynebacterium ammoniagenes* ATCC 6872. As a result, it was confirmed that the size of rih II gene encoding nucleoside hydrolase II was approximately 1326 bp (SEQ. ID. NO: 1). PCR was performed to obtain the gene fragment to construct a recombinant vector. The microorganism of *Corynebacterium* genus producing 5'-inosinic acid was transformed with the vector and the strain producing 5'-inosinic acid and inosine at high concentration was selected from the transformed strains. From the sequencing with chromosome of *Corynebacterium ammoniagenes* ATCC 6872, it was confirmed that the size of ushA gene encoding 5'-nucleotidase was approximately 2115 bp (SEQ. ID. NO: 2). PCR was performed to obtain the gene fragment to construct a recombinant vector. The microorganism of *Corynebacterium* genus producing 5'-inosinic acid and inosine was transformed with the vector and the strain producing inosine alone at high concentration was selected from the transformed strains.

The microorganism of the present invention is preferably obtained by transforming the microorganism of *Corynebacterium* genus producing 5'-inisinic acid with the recombinant vector containing rih II gene encoding nucleoside hycrolase II and the recombinant vector containing the ushA gene encoding 5'-nucleotidase. The recombinant vector containing nucleoside hydrolase II gene includes 500 bp of rih II structural gene sequence, while the recombinant vector containing 5-nucleotidase gene includes approximately 300 bp of promoter, ushA structural gene sequence and approximately 300 bp of terminator. The microorganism of the present invention is generated by disrupting the gene by inserting the recombinant vector containing rih II gene constructed using chromosome of the microorganism of *Corynebacterium* genus producing 5'-inosonic acid and by over-expressing ushA gene as a form of plasmid.

The recombinant vector containing nucleoside hydrolase II gene is constructed by the following processes; rih II gene obtained by PCR is separated and purified; and the purified gene is inserted into pCR2.1-TOPO vector by ligation. The recombinant vector herein is preferably pTOPO-rih II vector constructed by inserting a part of structural gene of nucleoside hydrolase II into pCR2.1-TOPO vector. The recombinant vector containing 5'-nucleotidase gene is constructed by the following processes; ushA gene obtained by PCR is digested with EcoRV and BamHI; and the gene fragment is inserted into the vector predigested with the same DNA restriction enzymes by using DNA T4 ligase. The applicable vector is not limited to specific one, and any conventional vector informed to those in the art can be used. However, pECCG117 vector [Biotechnology letters vol 13, No. 10, p. 721-726 (1991) or Korean Patent Publication No. 92-7401] is preferred and particularly pECCG117-ushA vector constructed by inserting ushA gene into peCCG117 vector is preferred.

Using the recombinant vector, for example pTOPO-rih II, linear DNA fragment can be inserted into the microorganism (for example, *Corynebacterium ammoniagenes* CJIP2401 (KCCM-10610)) by general electroporation and the microorganism is cultured in the medium containing kanamycin, the antibiotic used as a selection marker, followed by selection. The insertion of pTOPO-rih II vector in the selected transformed strain can be confirmed by PCR.

To over-express ushA gene in the selected transformed strain, linear DNA fragment is inserted into the selected transformed strain using pECCG117-ushA vector by electroporation and the strain is cultured in the medium containing chloramphenicol, the antibiotic used as a selection marker, followed by selection. The insertion of pECCG117-ushA vector in the selected transformed strain can be confirmed by PCR.

The microorganism of the present invention can be cultured in the conventional medium containing proper carbon source, nitrogen source, amino acids and vitamins, under aerobic condition with regulating temperature and pH properly.

As a carbon source, one of carbohydrates selected from the group consisting of glucose, fructose, and sterilized pre-treated molasses (molasses converted to reducing sugar). The nitrogen source is exemplified by such inorganic nitrogen source as ammonia, ammonium chloride and ammonium sulfate and such organic nitrogen source as peptone, NZ-amine, gravy, yeast extract, corn steep liquor, casein hydrolysate, fishes or decomposition product thereof, and defatted soybean cake or degradation products thereof. The medium herein can additionally include such inorganic compounds as potassium dihydrogen phosphate, dipotassium hydrogen phosphate, magnesium sulfate, iron sulfate, manganese sulfate and calcium sulfate, etc. In addition, vitamins and auxotrophic bases can be added as well. The culture is performed under aerobic condition by shaking-culture or submerger culture preferably at 20~40° C. pH is preferably regulated around neutral over the culture. The duration of the culture is preferably 4~5 days. The inosine accumulated by direct fermentation can be recovered by the conventional method.

According to the method of the present invention, inosine can be produced with high yield.

BRIEF DESCRIPTION OF THE DRAWINGS

The application of the preferred embodiments of the present invention is best understood with reference to the accompanying drawings, wherein:

FIG. 1 is a diagram illustrating the process of cloning of rih II gene fragment encoding nucleoside hydrolase II originated from the wild type *Corynebacterium ammoniagenes* ATCC 6872, and the cloned vector pTOPO-rih II.

FIG. 2 is a diagram illustrating the process of cloning of ushA gene fragment encoding 5'-nucleotidase originated from the wild type *Corynebacterium ammoniagenes* ATCC 6872, and the cloned vector pECCG117-ushA.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cloning of rih II Gene

In this example, 1326 bp rih II gene fragment (SEQ. ID. NO: 1) was amplified by PCR using chromosomal DNA of the wild type *Corynebacterium ammoniagenes* ATCC 6872 as a template with primers of oligonucleosides represented by SEQ. ID. NO: 3 and NO: 4 to construct the vector (rih II gene disruption vector) containing a part of rih II gene encoding nucleoside hydrolase II and an antibiotic marker. PCR was performed as follows; denaturation at 96° C. for 30 seconds, annealing at 52° C. for 30 seconds, and polymerization at 72° C. for 30 seconds (30 cycles). The amplified rih II gene fragment was cloned into the plasmid pCR2.1-TOPO (Invitrogen Co., USA). As a result, pTOPO-rih II vector was obtained. The cloning process of rih II gene fragment and the cloned vector pTOPO-rih II are illustrated in FIG. 1.

*Corynebacterium ammoniagenes* CJIP2401 (KCCM-10610) was transformed with the constructed pTOPO-rih II vector by electroporation. Then, single colonies growing on CM solid medium (gravy 10 g/L, yeast extract 10 g/L, bactopeptone 10 g/L, sodium chloride 2.5 g/L, bactoagar 1.7%, pH 7.0) containing kanamycin (25 ☐/L) were recovered.

The colonies were cultured in CM medium containing the same antibiotic, followed by separation of plasmid. The size of the plasmid was measured first and then colony PCR was performed using the primers comprising both ends of multi-cloning region of pCR2.1-TOPO to confirm transformation by measuring the size of the inserted DNA.

Primers used for inactivating rih II gene are as follows.

```
Primer rih II-F (SEQ. ID. NO: 3):
5'- TGCTGGCGATGCACTTGAAT -3

Primer rih II-B (SEQ. ID. NO: 4):
5'- TGTGCGACCAATGGTGGGGCC -3
```

The strain containing rih II gene selected above was named *Corynebacterium ammoniagenes* CJIG650, which was deposited at KCCM (Korean Culture Center of Microorganisms) of KFCC (Korean Federation of Culture Collection) on Dec. 15, 2006 (Accession No: KCCM 10828P).

Example 2

Cloning of ushA Gene

In this example, 2115 bp ushA gene fragment (SEQ. ID. NO: 2) was amplified by PCR using chromosomal DNA of the wild type *Corynebacterium ammoniagenes* ATCC 6872 as a template with primers of oligonucleosides represented by SEQ. ID. NO: 5 and NO: 6. PCR was performed as follows; denaturation at 96° C. for 30 seconds, annealing at 52° C. for 30 seconds, and polymerization at 72° C. for 30 seconds (30 cycles). The obtained gene fragment was digested with EcoRV and BamHI. The gene fragment was ligated to linear pECCG117 vector digested with the same DNA restriction enzymes by using DNA T4 ligase. As a result, pECCG117-ushA vector was obtained. The cloning process of ushA gene fragment and the cloned vector pECCG117-ushA are illustrated in FIG. 2.

The mutant strain prepared in Example 1 was transformed with the constructed pECCG117-ushA vector by electroporation. Then, single colonies growing on CM solid medium (gravy 10 g/L, yeast extract 10 g/L, bactopeptone 10 g/L, sodium chloride 2.5 g/L, bactoagar 1.7%, pH 7.0) containing chloramphenicol (7.5 ☐/L) were recovered. The colonies were cultured in CM medium containing the same antibiotic, followed by separation of plasmid. The size of the plasmid was measured first and then colony PCR was performed using the primers comprising both ends of multi-cloning region of pECCG117 to confirm transformation by measuring the size of the inserted DNA.

Primers used for over-expressing ushA gene are as follows.

```
Primer ushA -F (SEQ. ID. NO: 5):
5'- GTGTCTAAGTTTCGCCGTTTTGGC -3

Primer ushA -B (SEQ. ID. NO: 6):
5'- GCCGGATCCCTAGAATTTGATGTGGCTAACCTCG -3
```

The strain containing ushA gene selected above was named *Corynebacterium ammoniagenes* CJIG651, which was deposited at KCCM (Korean Culture Center of Microorganisms) of KFCC (Korean Federation of Culture Collection) on Dec. 15, 2006 (Accession No: KCCM 10829P).

Example 3

Fermentation Test in Erlenmeyer Flask 3 ml of seed medium was distributed in test tubes of 18 mm in diameter, which were sterilized by autoclave. *Corynebacterium ammoniagenes* CJIG650 (KCCM-10828P), CJIG651 (KCCM-10829P) and the parent strain (KCCM-10610) were inoculated in the test tubes respectively, followed by shaking culture at 30° C. for 24 hours to prepare seed culture solution. 27 ml of fermentation medium was distributed in 500 ml Erlenmeyer flask for shaking, which was sterilized by autoclave at 120° C. for 10 minutes. After inoculation of 3 ml of the seed culture solution, culture was performed for 4~5 days. RPM was regulated as 200 and temperature was set at 32° C. and pH was regulated as 7.2.

The compositions of the seed medium and the fermentation medium are as follows.

Seed medium Glucose 5%, Peptone 0.5%, Gravy 0.5%, Yeast extract 1%, Sodium chloride 0.25%, Adenine 100 mg/l, Guanine 100 mg/l, pH7.2

Flask fermentation medium: Sodium glutamate 0.1%, Ammonium chloride 1%, Magnesium sulfate 1.2%, Calcium chloride 0.01%, Iron sulfate 20 mg/l, Manganese sulfate 20 mg/l, Zinc sulfate 20 mg/l, Copper sulfate 5 mg/l, L-cysteine 23 mg/l, Alanine 24 mg/l, Nicotinic acid 8 mg/l, Biotin 45 □ /l, Thiamine HC15 mg/l, Adenine 30 mg/l, Phosphoric acid (85%) 1.9%, Reducing sugar 8% converted from the mixture of fructose, glucose and molasses.

The accumulations of inosinic acid (IMP) or inosine in CJIG650 (KCCM-10828P), CJIG651 (KCCM-10829P) and the parent strain (KCCM-10610) culture media were compared one another. And the results are shown in Table 1. As shown in Table 1, only inosinic acid was accumulated in the parent strain KCCM-10610) culture medium and inosine was not accumulated at all therein. However, the strains of the present invention, CJIG650 (KCCM-10828P) produced inosinic acid and inosine at high concentration, and the strain CJIG651 (KCCM-10829P) produced inosine at high concentration.

Therefore, the strains of the present invention CJIG650 (KCCM-10828P) and CJIG651 (KCCM-10829P) were confirmed to be the strains capable of producing inosine at high concentration.

TABLE 1

| Strain | IMP concentration (g/L) | Inosine concentration (g/L) |
| --- | --- | --- |
| Control (KCCM-10610) | 14.1 | — |
| CJIG650 | 8 | 4 |
| CJIG651 | — | 8.3 |

INDUSTRIAL APPLICABILITY

As explained hereinbefore, the *Corynebacterium ammoniagenes* CJIG650 and CJIG651 prepared by inactivating the gene encoding nucleoside hydrolase II and by reinforcing the gene encoding 5'-nucleotidase can produce inosine at high concentration Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A recombinant *Corynebacterium ammoniagenes*, producing inosine by inactivation of the gene encoding nucleoside hydrolase II having the nucleotide sequence represented by SEQ ID NO: 1 and by over-expression of the gene encoding 5'-nucleotidase represented by SEQ ID NO: 2.

2. The recombinant *Corynebacterium ammoniagenes* according to claim 1, wherein the inactivation is induced by transforming the microorganism with the vector comprising a part of the sequence represented by SEQ ID NO: 1 and an antibiotic marker.

3. The recombinant *Corynebacterium ammoniagenes* according to claim 1, wherein the recombinant *Corynebacterium ammoniagenes* is *Corynebacterium ammoniagenes* CJIG651 (KCCM-101829P).

4. A recombinant *Corynebacterium ammoniagenes*, which is derived from *Corynebacterium ammoniagenes* CJIP2401 (KCCM-10610), producing inosinic acid and inosine by inactivation of the gene encoding nucleoside hydrolase II having the nucleotide sequence represented by SEQ ID NO:1, wherein the recombinant *Corynebacterium ammoniagenes* is *Corynebacterium ammoniagenes* CJIG650 (KCCM-101828P).

* * * * *